(12) United States Patent
Kawamura

(10) Patent No.: US 6,620,622 B1
(45) Date of Patent: Sep. 16, 2003

(54) METHOD OF POLARIMETRY AND METHOD OF URINALYSIS USING THE SAME

(75) Inventor: Tatsurou Kawamura, Kyotanabe (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 507 days.

(21) Appl. No.: 09/604,406

(22) Filed: Jun. 27, 2000

(30) Foreign Application Priority Data

Jun. 29, 1999 (JP) .......................................... 11-184272

(51) Int. Cl.⁷ ............................. G01N 21/75; G01J 4/00
(52) U.S. Cl. ....................... 436/164; 356/364; 356/367; 356/368; 250/225
(58) Field of Search .......................... 436/164; 356/364, 356/367, 368; 250/225

(56) References Cited

U.S. PATENT DOCUMENTS

| 3,312,141 A | | 4/1967 | Cary |
| 4,988,199 A | * | 1/1991 | Paul ............................ 356/368 |
| 6,036,922 A | * | 3/2000 | Kawamura et al. ...... 422/82.09 |
| 6,046,804 A | * | 4/2000 | Kawamura et al. ......... 356/244 |
| 6,166,807 A | * | 12/2000 | Kawamura et al. ......... 356/364 |
| 6,297,057 B1 | * | 10/2001 | Kawamura et al. ............ 436/86 |

FOREIGN PATENT DOCUMENTS

EP 0 805 352 11/1997

OTHER PUBLICATIONS

"Numerical Recipes in C"1992, Cambridge University Press, Chapter 15, Modeling of Data, second edition, pp. 656–666.

* cited by examiner

Primary Examiner—Jill Warden
Assistant Examiner—LaToya Cross
(74) Attorney, Agent, or Firm—McDermott, Will & Emery

(57) ABSTRACT

According to the present invention, in a polarimetry for allowing a light to be incident upon a specimen with a spontaneous optical active substance, a polarized light is allowed to be incident upon the specimen while microvibrating the plane of vibration; a component having a specific plane of vibration is detected out of the polarized light through the specimen; a component with a certain angular frequency is extracted; and an angle of rotation attributed to the specimen is calculated based on 3 or more groups of data including a relative angle formed between the plane of vibration of the light incident upon the specimen and the plane of vibration of the light, and an intensity of the component with the angular frequency obtained at the relative angle. Consequently, the influence of noises mixed due to bubbles, particles and the like can be eliminated, thereby achieving a stable and highly accurate measurement in a shorter time.

19 Claims, 6 Drawing Sheets

F I G. 1
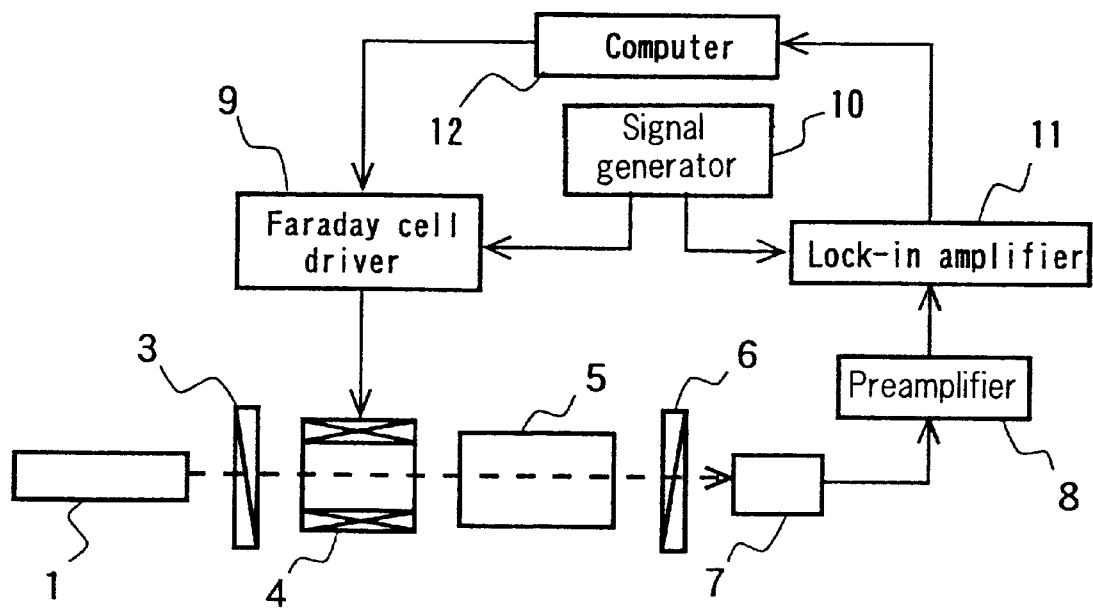

F I G. 2
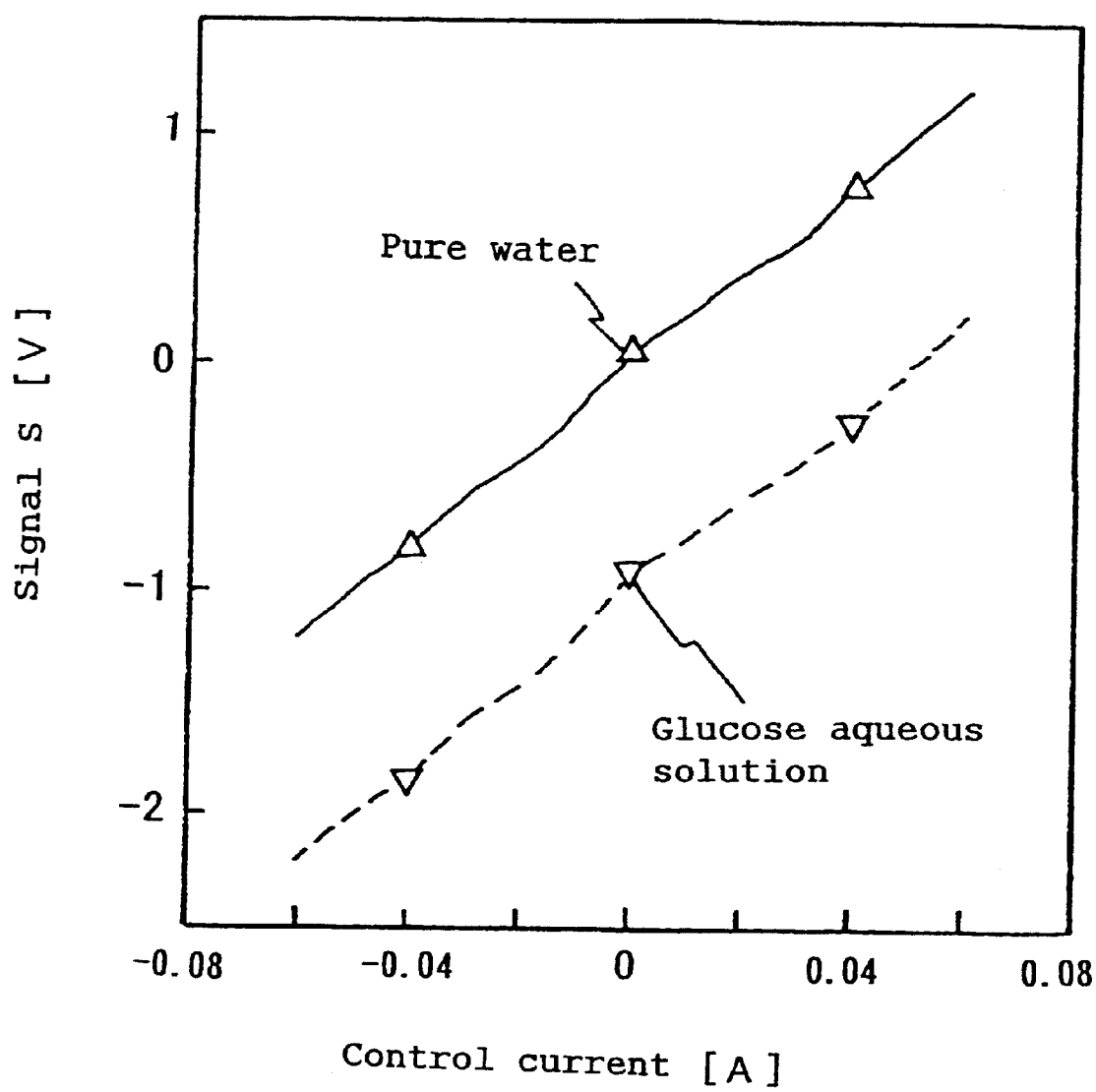

METHOD OF POLARIMETRY AND METHOD OF URINALYSIS USING THE SAME

BACKGROUND OF THE INVENTION

The present invention relates to a method of polarimetry for use in the identification, examination on purity, determination of the concentration and the like of a solute in a liquid specimen, and a method of urinalysis using the same.

A polarimeter is employed as an optical rotation detecting type saccharimeter for detecting the concentrations of fructose, sucrose, glucose, and the like contained in an aqueous solution. It can also determine especially the concentrations of optical active substances such as glucose and protein in a urine. Therefore, it is expected to come into wide use as a urinalysis equipment which requires no consumable articles such as test papers.

FIG. 6 shows a conceptual constitution of one example of conventional polarimeters. The polarimeter is for determining the magnitude of spontaneous optical rotatory power, i.e., an angle of rotation attributed to a spontaneous optical rotatory power of a spontaneous optical active substance in a specimen to be detected. In concrete, the angle of spontaneous optical rotation is determined based on an angle of magnetorotation (compensated value) by an optical Faraday effect when the spontaneous optical rotation attributed to the spontaneous optical active substance is canceled (compensated) by the magnetorotation.

A semiconductor laser module 21 configured with a sodium lamp, a band-pass filter, a lens, a slit, and the like projects a substantially parallel light composed of a sodium D ray having a wavelength of 589 nm. A polarizer 23 transmits only a component that has a specific plane of vibration out of the light projected from the semiconductor laser module 21. A sample cell 25 for holding a specimen to be detected has a pair of mutually opposing transparent transmission surfaces, and is arranged so that the light projected from the semiconductor laser module 21 can transmit through the inside thereof. An analyzer 26 transmits only a component that has another specific plane of vibration out of the light transmitted through the sample cell 25. The relative angle $\Theta$ formed between the transmission axis of the polarizer 23 and the transmission axis of the analyzer 26 is fixed at $\pi/2$. A photosensor 27 detects the component transmitted through the analyzer 26 out of the light projected from the semiconductor laser module 21. A Faraday cell 24 modulates and controls the plane of vibration of the light projected from the semiconductor laser module 21 based on a modulation signal outputted from a signal generator 30 and a control signal outputted from a computer 22. The Faraday cell 24 is driven by a Faraday cell driver 29. A lock-in amplifier 28 performs a phase sensitive detection on the output signal from the photosensor 27 by using the modulation signal outputted from the signal generator 30 as a reference signal. The computer 22 calculates the angle of rotation attributed to the specimen to be detected accommodated in the sample cell 25 based on the control signal, and the output signal from the lock-in amplifier 28.

As described above, by sweeping the angle of the plane of vibration by the Faraday cell, it becomes possible to achieve simplification and compactness thereof as compared with apparatuses using other means for modulating the plane of vibration.

Below, the principle of the conventional polarimeter will be described.

The Faraday cell 24 modulates the plane of vibration of the light projected from the semiconductor laser module 21 and transmitted through the polarizer 23 with an amplitude of "$\delta$" and an angular frequency of "$\omega$". In this step, the intensity "I" of the light that has reached the photosensor 27 is represented by the following equation (1):

$$I = T \times I_0 \times \{\cos[\Theta - \alpha + \beta + \delta \times \sin(\omega \times t)]\}^2 \quad (1)$$

where T: transmittance of the specimen,
$I_0$: intensity of the light incident upon the specimen,
$\Theta$: relative angle formed between the transmission axis of the polarizer 23 and the transmission axis of the analyzer 26,
$\alpha$: angle of rotation attributed to the specimen,
$\beta$: angle of rotation of light due to the Faraday cell 24, and
t: time.

It is noted that the transmission loss and the reference loss of the sample cell 25 and the analyzer 26 respectively are ignored.

Since the relative angle $\Theta$ between the transmission axis of the polarizer 23 and the transmission axis of the analyzer 26 is $\pi/2$, the following equation (2) is given from the equation (1).

$$I = T \times I_0 \times \{\sin[\beta - \alpha + \delta \times \sin(\omega \times t)]\}^2 \quad (2)$$

In case of $\beta - \alpha = 0$, in other words, when it is assumed that the angle of rotation attributed to the specimen is canceled (compensated) by the angle of rotation due to the Faraday cell 24, the equation (2) is expressed as the following equation (3):

$$I = (1/2) \times T \times I_0 \times \{1 - \cos[2 \times \delta \times \sin(\omega \times t)]\} \quad (3)$$
$$= (1/2) \times T \times I_0 \times \{1 - [J_0(2 \times \delta) +$$
$$2 \times J_2(2 \times \delta) \times \cos(2 \times \omega \times t) + \ldots ]\}$$

where $J_n(X)$ is an nth-degree Bessel function.

The equation (3) indicates that the intensity "I" of the light detected by the photosensor 27 does not contain the frequency component $\omega$ of the modulation signal alone.

When it is assumed that the angle of rotation attributed to the specimen and the amplitude of the modulation are small, that is, $|\beta - \alpha| << 1$, and $\delta << 1$, the equation (3) is approximated to the following equation (4):

$$I \cong T \times I_0 \times (\beta - \alpha + \delta \times \sin(\omega \times t))^2 \quad (4)$$
$$= T \times I_0 \times \{(\beta - \alpha)^2 + 2(\beta - \alpha) \times \delta \times \sin(\omega \times t) +$$
$$[\delta \times \sin(\omega \times t)]^2\}$$
$$= T \times I_0 \times \{(\beta - \alpha)^2 + 2(\beta - \alpha) \times \delta \times \sin(\omega \times t) +$$
$$[\delta^2/2 \times \{1 - \cos(2 \times \omega \times t)\}]\}$$

This indicates that the output signal "I" from the photosensor 27 contains components with angular frequencies of 0 (DC), "$\omega$", and "$2\times\omega$", respectively. By the phase sensitive detection of the value "I" using the modulation signal as a reference signal in the lock-in amplifier 28, it is possible to pick up the component of the angular frequency "$\omega$", i.e., the signal "S" shown by the following equation (5):

$$S = T \times I_0 \times 2 \times (\beta - \alpha) \times \delta \quad (5)$$

This signal "S" equals zero only when $\beta = \alpha$. This point is the extinction point. In the process of rotating the plane of vibration of light by the Faraday cell 24, in other words, sweeping "β", the value of "β" when "S" becomes zero corresponds to the angle "α" of rotation. The same is also true for the case where this process is considered based on the equation (3). Namely, upon the phase sensitive detection of the value "I", the output "I" from the photosensor 27 becomes zero when β=α.

As described above, by modulating the angle of plane of vibration of light, it is possible to pick up only the signal "S" of the modulated frequency component selectively while separating the signal from noises attributed to an intensity of the light source, a fluctuation in the power source, a radiation and the like, thereby deriving a signal with a high S/N ratio. Therefore, the extinction point can be determined accurately by using this value of the signal "S", and hence the angle "α" of rotation can be determined with high accuracy.

However, in the above-described polarimetry, it is required to detect the output signal from the lock-in amplifier 28 while continuously changing β at a minute angular velocity so that the signal "S" becomes zero. For this reason, a large number of measurement points are required, and a longer duration of time is also required even by automation. Further, when the feedback control is conducted based on the measured value at each measurement point, the presence of bubbles, particles, and the like on the optical path for the light transmitted through the inside of the sample cell 25 entails fluctuations of the measured value. Therefore, an appropriate loop cannot be constructed, and hence a still longer measuring duration of time is required.

It is therefore an object of the present invention to provide a method of polarimetry and a method of urinalysis capable of solving the above-mentioned conventional problems and eliminating the influences exerted by the noises mixed due to bubbles, particles, and the like, and permitting a stable and highly accurate measurement in a short duration of time.

BRIEF SUMMARY OF THE INVENTION

Apparent from the above equation (5), the relation between the intensity of the component with an angular frequency of ω and the relative angle formed between the transmission axis of the polarizer and the transmission axis of the analyzer is expressed by a linear function in the vicinity of the extinction point. In the present invention, by using this principle, the extinction point is determined from a linear regression formula (regression line) derived from the mutually different three or more relative angles and the intensities of the components whose angular frequencies are ω at respective relative angles.

Specifically, the present invention provides, as a first embodiment, a method of polarimetry for allowing a light to be incident upon a specimen to be detected containing a spontaneous optical active substance, and determining an optical rotation attributed to the spontaneous optical active substance when the light transmits through the specimen, comprising the steps of:

(a) allowing a polarized light having a known plane of vibration to be incident upon the specimen while micro-vibrating the plane of vibration by a modulation signal with an angular frequency of ω;

(b) detecting a component having a specific plane of vibration out of the polarized light transmitted through the specimen by a photosensor;

(c) extracting a component with an angular frequency of ω out of an output signal from the photosensor by phase sensitive detection using the modulation signal as a reference signal; and (d) calculating an angle of rotation attributed to the specimen based on 3 or more groups of data including a relative angle formed between a plane of vibration of the light incident upon the specimen and the specific plane of vibration of the light detected by the photosensor, and an intensity of the component with an angular frequency of ω obtained at the relative angle.

In the step (a), it is effective that the relative angle is varied by continuously rotating the plane of vibration of the polarized light incident upon the specimen.

Further, in the step (a), it is also effective that the relative angle is varied by discretely changing the plane of vibration of the polarized light incident upon the specimen.

In the step (d), it is effective that a linear regression formula is formed based on the data by using the relative angle as a criterion variable and using the intensity of the component with an angular frequency of ω as a dependent variable, and the angle of rotation attributed to the specimen is calculated based on the obtained regression formula.

Further, in the step (a), it is also effective that the relative angle is varied by rotating the plane of vibration of the polarized light incident upon the specimen by an optical Faraday effect.

Still further, in the step (d), it is effective that a linear regression formula is formed based on the data by using a magnitude of a magnetic field for obtaining the relative angle or a current amount for generating the magnetic field as a criterion variable and using the intensity of the component with an angular frequency of ω as a dependent variable, and the angle of rotation attributed to the specimen is calculated based on the obtained regression formula.

Further, the present invention also provides, as a second embodiment, a method of polarimetry for allowing a light to be incident upon a specimen to be detected containing a spontaneous optical active substance and a magneto-optical active substance, and applying a magnetic field to the specimen, thereby rotating a plane of vibration of the light transmitting though the specimen by an optical Faraday effect, and determining an optical rotation due to the spontaneous optical active substance when the light transmits through the specimen based on the magnitude of rotation of the light caused by the application of the magnetic field, comprising the steps of:

(a) allowing a polarized light having a known plane of vibration to be incident upon the specimen while micro-vibrating the plane of vibration by a modulation signal with an angular frequency of ω;

(b) detecting a component having a specific plane of vibration out of the polarized light transmitted through the specimen by a photosensor;

(c) extracting a component with an angular frequency of ω out of an output signal from the photosensor by phase sensitive detection using the modulation signal as a reference signal; and (d') calculating an angle of rotation attributed to the specimen based on 3 or more groups of data including a magnitude of the magnetic field and an intensity of the component with an angular frequency of ω obtained at the magnitude of the magnetic field.

In the step (a), it is effective that the plane of vibration of the light is continuously rotated by the optical Faraday effect.

Further, in the step (a), it is also effective that the plane of vibration of the light is discretely changed by the optical Faraday effect.

Further, in the step (d'), it is effective that, a linear regression formula is formed based on the data, by using the magnitude of the magnetic field or the current amount for generating the magnetic field as a criterion variable and using the intensity of the component with an angular frequency of ω as a dependent variable, and that an angle of rotation attributed to the specimen is calculated based on the regression formula obtained.

Further, in the method of polarimetry, it is effective that the regression formula is calculated by using a least squares method.

Furthermore, it is effective to further comprise a step of estimating the measurement to be effective when a reliability of the regression formula is higher than a predetermined value.

At this step, it is effective to use a sum of squares of residuals "$S_E$" (equation (6)), a value "D" (equation (8)) obtained by dividing the sum of squares of residuals "$S_E$" by the sum of squares of the intensity values of the component with an angular frequency of ω, which is obtained by substituting the data corresponding to the criterion variable of the regression formula, or a correlation coefficient "R" (equation (7)) expressed as each of the following formulae.

$$S_E = \sum_{i=1}^{n} \{Y_i - (a+bX_i)\}^2 \quad (6)$$

$$R = \frac{\sum_{i=1}^{n} [(X_i - \overline{X}) \times (Y_i - \overline{Y})]}{\sqrt{\sum_{i=1}^{n} (X_i - \overline{X})^2 \times \sum_{i=1}^{n} (Y_i - \overline{Y})^2}} \quad (7)$$

$$D = \frac{S_E}{\sum_{i=1}^{n} (a+bX_i)^2} \quad (8)$$

where the regression formula is expressed as Y=a+bX, $X_i$ (i=1 to n) is the data for the criterion variable "X" of the regression formula, $Y_i$ (i=1 to n) is the data for the dependent variable "Y" of the regression formula, $\overline{X}$ is the mean value of $X_i$, and $\overline{Y}$ is the mean value of $Y_i$.

Further, according to the method of polarimetry, when a specimen to be detected is a urine, it is possible to provide a method of urinalysis for efficiently detecting the concentration of the spontaneous optical active substance in the urine.

BRIEF DESCRIPTION OF THE SEVERAL VIEWS OF THE DRAWING

FIG. 1 is a block diagram showing the configuration of a polarimeter used in one embodiment of the present invention.

FIG. 2 is a characteristic diagram showing the relation between a control signal to be injected into the Faraday cell obtained in the embodiment and the intensity of a signal "S" outputted from a lock-in amplifier.

DETAILED DESCRIPTION OF THE INVENTION

Figure 3:
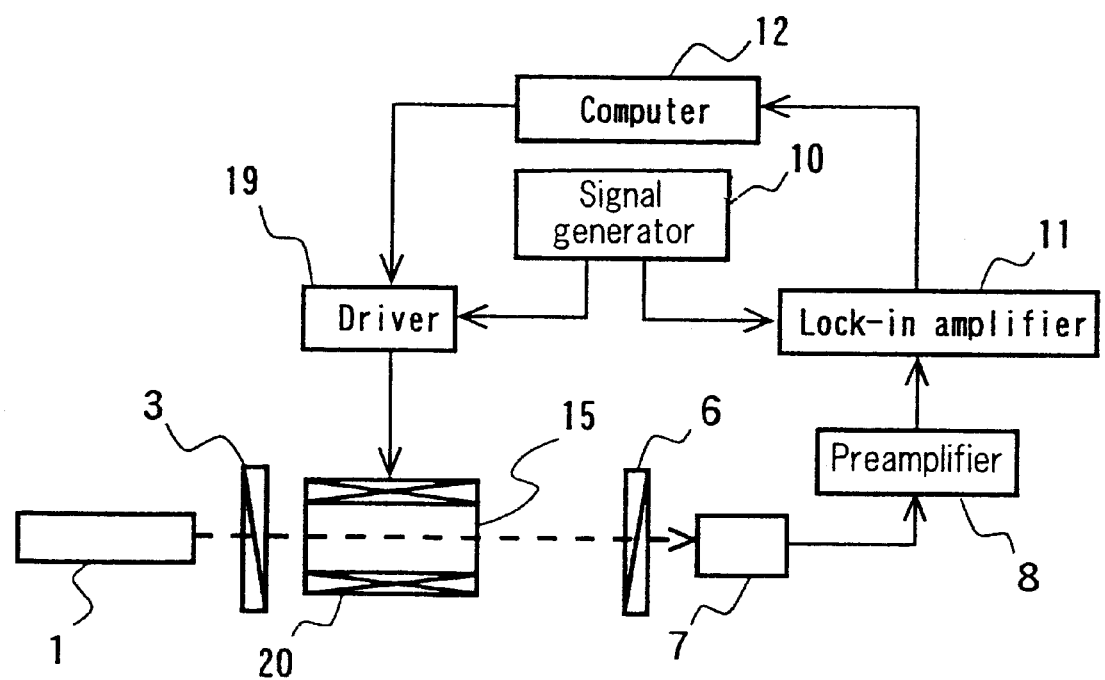
FIG. 3 is a block diagram showing the configuration of the polarimeter used in another embodiment of the present invention.

A first method of polarimetry according to the present invention is a method of polarimetry for allowing a light to be incident upon a specimen to be detected containing a spontaneous optical active substance, and determining the optical rotation due to the spontaneous optical active substance when the light transmits through the specimen, comprising the steps of:

(a) allowing a polarized light having a known plane of vibration to be incident upon the specimen while micro-vibrating the plane of vibration by a modulation signal with an angular frequency of ω;

(b) detecting a component having a specific plane of vibration out of the polarized light transmitted through the specimen by a photosensor;

(c) extracting a component with an angular frequency of ω expressed as the equation (5) out of an output signal from the photosensor by phase sensitive detection using the modulation signal as a reference signal; and (d) calculating an angle of rotation attributed to the specimen based on 3 or more groups of data including a relative angle formed between the plane of vibration of the light incident upon the specimen and the plane of vibration of the light to be detected by the photosensor, and an intensity of the component with an angular frequency of o obtained at the relative angle.

In the present invention, from the data including the relative angle formed between the plane of vibration of the light incident upon the specimen and the plane of vibration of the light detected by the photosensor, and the intensity of the component whose angular frequency detected at the detection is ω, a linear regression formula representing the relation therebetween is formed. Then, the angle of rotation attributed to the specimen is calculated using such a linear regression formula.

Of course, the relative angle is not required to be directly used. When the plane of vibration of the light incident upon the specimen is rotated by the optical Faraday effect, i.e., magnetorotation, the magnitude of the magnetic field for obtaining the relative angle, or the amount of current for generating the magnetic field may also be used in place of the relative angle. If the magnitude of the magnetic field or the amount of current when the extinction point appears is found, it is possible to easily calculate the angle of rotation attributed to the specimen using a known formula.

Further, the relative angle formed between the plane of vibration of the light incident upon the specimen and the plane of vibration of the light detected by the photosensor may be varied by rotating either one plane of vibration. For example, the plane of vibration of the incident light may be continuously rotated. Alternatively, since a continuous measurement is not required in the present invention, the plane of vibration of the incident light may also be discretely varied.

According to the present invention, the configuration of a circuit to be used can be simplified because of no necessity for continuously varying "β" shown in the respective formulae. Further, it is possible to predetermine wide concentration range of the specimen because of no necessity for directly determining the extinction point.

Further, the present invention described above can also be applied to the measuring method in which the angle of rotation is determined based on the magnitude of magnetorotation due to the optical Faraday effect attributed to the magneto-optical active substance in the specimen, caused by directly applying a magnetic field to the specimen.

Namely, a second method of polarimetry according to the present invention is a method of polarimetry for allowing a light to be incident upon a specimen to be detected containing a spontaneous optical active substance and a magneto-optical active substance and applying a magnetic field to the specimen, thereby rotating the plane of vibration of the light transmitting though the specimen by the optical Faraday effect, and determining the optical rotation due to the spontaneous optical active substance when the light transmits through the specimen based on the magnitude of rotation of the light caused by the application of the magnetic field, comprising the steps of:

(a) allowing a polarized light having a known plane of vibration to be incident upon the specimen while micro-vibrating the plane of vibration by a modulation signal with an angular frequency of $\omega$;

(b) detecting a component having a specific plane of vibration out of the polarized light transmitted through the specimen by a photosensor;

(c) extracting a component with an angular frequency of $\omega$ out of the output signal from the photosensor by phase sensitive detection using the modulation signal as a reference signal; and (d') calculating an angle of rotation attributed to the specimen based on 3 or more groups of data including the magnitude of the magnetic field and the intensity of the component with an angular frequency of $\omega$ obtained at the magnitude of the magnetic field.

Herein, a linear regression formula is formed based on a combination of the magnitude of the magnetic field or the amount of current, and the intensity of the component whose angular frequency is $\omega$, by using the one as a variable for the other. The angle of rotation attributed to the specimen can be calculated based on the regression formula thus obtained. For example, a linear regression formula is calculated by using the magnitude of the magnetic field or the amount of current for generating the magnetic field as a criterion variable, and using the intensity of the component whose angular frequency is $\omega$ as a dependent variable. Then, the angle of rotation attributed to the specimen can be calculated based on the regression formula thus obtained.

The magnitude of rotation of the light due to the optical Faraday effect may be continuously or discretely varied.

For calculation of the above-described regression formula, for example, the least squares method is used.

The reliability of the regression formula can be evaluated using the sum of squares of residuals "$S_E$" shown in the following equation (6) as an index. Then, when it is lower than a predetermined value, the angle of rotation obtained may be estimated as being effective. Consequently, it is possible to conduct the measurement with a higher reliability with eliminating results which have received the influences of noises.

Further, the closer to 1 the correlation function "R" shown in the equation (7) is, the more reliable measurement becomes possible with eliminating results which have received the influences of noises.

As shown in the following equation (8), by using the value "D" obtained by dividing the sum of squares of residuals "$S_E$" by the sum of the square of the value of the dependent variable obtained by substituting the data corresponding to the criterion variable of the regression formula (i.e., the calculated value of the signal "S"), it is possible to eliminate the influences such as the light transmittance of the sample cell.

$$S_E = \sum_{i=1}^{n} \{Y_i - (a+bX_i)\}^2 \quad (6)$$

$$R = \frac{\sum_{i=1}^{n}[(X_i - \overline{X}) \times (Y_i - \overline{Y})]}{\sqrt{\sum_{i=1}^{n}(X_i - \overline{X})^2 \times \sum_{i=1}^{n}(Y_i - \overline{Y})^2}} \quad (7)$$

$$D = \frac{S_E}{\sum_{i=1}^{n}(a+bX_i)^2} \quad (8)$$

where the regression formula is expressed as Y=a+bX, $X_i$ (i=1 to n) is the data for the criterion variable "X" of the regression formula, $Y_i$ (i=1 to n) is the data for the dependent variable "Y" of the regression formula, $\overline{X}$ is the mean value of $X_i$, and $\overline{Y}$ is the mean value of $Y_i$.

It is noted that the influences of noises mixed into the signal can also be reduced by increasing the number of the measurement points. In particular, when the measurement is conducted at a large number of measurement points, for example, the data for every measurement point can also be checked up with the regression formula calculated from the previously obtained data to determine whether the data at the measurement point is employed or eliminated.

The method of polarimetry according to the present invention can be applied to a urinalysis for detecting the concentrations of spontaneous optical active substances such as glucose and albumin contained in a urine used as the specimen.

Below, the preferred embodiments of the present invention are explained in details by reference to drawings.

EXAMPLE 1

FIG. 1 schematically shows the configuration of a polarimeter of this example according to the present invention.

A semiconductor laser module 1 projects a substantially parallel light having a wavelength of 780 nm and an intensity of 3.0 mW. A polarizer 3 transmits only a specific polarized component having a plane of vibration coincident with the transmission axis thereof, for example, a component having a plane of vibration parallel to the plane of a sheet of paper, out of the light projected from the semiconductor laser module 1. A Faraday cell 4 is provided in the back of the polarizer 3. The Faraday cell 4 comprises a light transmitting core member made of, for example, a flint glass, and a solenoid coil for generating a magnetic field along the advancing direction of the light passing through the core member. A Faraday cell driver 9 superimposes a modulation signal for modulating a magnetic field generated on a control signal for generating the magnetic field in the Faraday cell 4, and outputs it to the Faraday cell 4. The Faraday cell 4 generates a magnetic field by a signal from the Faraday cell driver 9, and rotates the plane of vibration of the light transmitting therethrough due to the optical Faraday effect.

A sample cell 5 for accommodating a specimen is arranged so that the light projected by the semiconductor laser module 1 and transmitted through the polarizer 3 and the Faraday cell 4 transmits through the inside thereof. The substantial optical path length of the sample cell 5 is 50 mm. An analyzer 6 is arranged with the polarizer 3 in a so-called crossed nicols state, and selectively transmits the light of the component having a plane of vibration orthogonal to that of the light transmitting through the polarizer 3. A photosensor 7 detects the light transmitted through the analyzer 6.

A preamplifier 8 amplifies the output from the photosensor 7, and outputs it to a lock-in amplifier 11. A signal generator 10 outputs a modulation signal to the Faraday cell driver 9. The lock-in amplifier 11 conducts a phase sensitive detection on the output signal from the preamplifier 8 by using the modulation signal outputted to the Faraday cell 4 as a reference signal, and outputs the signal "S" expressed as the equation (5) to a computer 12. The computer 12 outputs a control signal to the Faraday cell driver 9, while calculating the angle of rotation based on the output signal from the lock-in amplifier 11.

The angles of rotation of pure water and a glucose aqueous solution with a concentration of 1000 mg/dl were measured, respectively, by using the aforesaid polarimeter.

While sweeping the control current to be supplied to the Faraday cell 4 in a range from −0.06 A to 0.06 A for 60 seconds, a modulation current with a frequency of 1.3 kHz and an amplitude of 0.001 A is superimposed thereon. The relation between the control current and the output from the lock-in amplifier 11, i.e., the signal "S" at this step is shown in FIG. 2 by a solid line (pure water) and a dashed line (glucose aqueous solution). In the case of the pure water, since pure water exhibits no optical activity, the output from the lock-in amplifier 11 becomes zero when the current injected into the Faraday cell is 0 A. Meanwhile, in the case of the glucose aqueous solution with the aforesaid concentration, it is previously set so that the output becomes zero at 0.051 A. The control current is supplied to the solenoid coil of the Faraday cell 4 for forming a magnetic field. Therefore, the magnitude of rotation of the plane of vibration occurring in the light transmitting through the Faraday cell 4 at this current value coincides with the angle of rotation attributed to a spontaneous optical active substance (the magnitude of spontaneous optical rotation).

Herein, the time constant of the lock-in amplifier 11, that is, the integral action time of the detection signal was set as follows. First, the time constant was set to be sufficiently shorter as compared with the sweep time, about 3 milliseconds, which was longer than the period of the modulation signal, and the control current was swept to obtain a linear characteristic curve showing the relation between the control current and the output signal "S" from the lock-in amplifier 11 as shown in FIG. 2. Then, by using a time constant of 100 milliseconds given immediately before deviating from the previously obtained curve, the time constant being determined by gradually increasing the time constant while seeking the similar relation, the following measurement was carried out. Herein, the wording "deviating" denotes "a reduction in gradient of the curve". By performing these steps, it is possible to achieve the highest S/N ratio with respect to the time required for sweeping.

Further, although the characteristic curve showing the relation between the control signal and the signal "S" is a straight line as shown in the equation (5) in principle, it will not be a straight line because of the mixing of various noises in actuality. The control currents when the signal "S" becomes zero are read from the characteristic curve actually obtained are 0.002 A and 0.05 A for the pure water and the glucose aqueous solution, respectively. That is, there is observed the error due to the mixing of a noise.

The signal "S" when the control currents are −0.04 A, 0, and 0.04 A are shown in Table 1.

TABLE 1

| Control current [A] | Signal "S" [V] | |
|---|---|---|
| | Pure water | Glucose aqueous solution |
| −0.04 | −0.82 | −1.85 |
| 0 | 0.05 | −0.92 |
| 0.04 | 0.78 | −0.26 |

Herein, if it is assumed that the control current is a criterion variable "X", and the signal "S" is a dependent variable "Y", the regression lines shown in the following equations (9) and (10) are obtained by the least squares method for the pure water and the glucose aqueous solution, respectively.

Pure water: $Y = 0.00333 + 20 \times X$ (9)

Glucose aqueous solution: $Y = -1.01 + 19.9 \times X$ (10)

The values of "X" when "Y" becomes zero are determined from the resulting regression lines to be −0.000167 A and 0.0508 A for the pure water and the glucose aqueous solution, respectively. Thus, the values obtained are closer to the respective true values previously set than the values obtained by directly reading the extinction points.

The sum of squares of residuals is found to be $3.27 \times 10^{-3}$ from the regression line shown in the equation (9) and the data for the pure water shown in Table 1. Meanwhile, the sum of squares of residuals is found to be $1.22 \times 10^{-2}$ from the regression line shown in the equation (9) and the data for the glucose aqueous solution shown in Table 1.

The data in case where a large noise is mixed into the signal during measuring the angle of rotation attributed to the glucose aqueous solution is shown in Table 2.

TABLE 2

| Control current [A] | Signal "S" [V] |
|---|---|
| −0.04 | −2.05 |
| 0 | −0.92 |
| 0.04 | −0.26 |

In Table 2, a noise is mixed at a control current of −0.04 A. The regression line obtained by using the data is expressed as the following equation (11):

$Y = -1.08 + 22.4 \times X$ (11)

According to the equation (8), the control current "X" when the output signal "S" from the lock-in amplifier 11, indicated with "Y", becomes zero is 0.0482 A. Comparison of this value with the predetermined value indicates that there is obviously observed the influence of mixing of a noise on the calculated value. The sum of squares of residuals at this time is $8.62 \times 10^{-2}$. This value is obviously greater than the value obtained by using the data shown in Table 1, indicating a low fit with respect to the regression line.

Then, the sum of squares of residuals is used as an index for evaluating the reliability of the regression formula, in other words, the fit between the regression formula and the measured data. For example, if this value is greater than a predetermined value, the error factor, i.e., noise is considered to be contained in the measured data in an amount exceeding the allowable level, and the measurement is nullified to conduct another measurement. Consequently, a measurement with high accuracy can be ensured. As for the above-mentioned glucose aqueous solution, when the sum of squares of residuals is greater than, for example, $2.0 \times 10^{-2}$, the measurement may be nullified.

EXAMPLE 2

A polarimeter of this example according to the present invention is shown in FIG. 3.

The polarimeter of this example magneto-optically rotates the light projected from the semiconductor laser module 1 by a solenoid coil 20 wound around a sample cell 15 in place of the Faraday cell 4 used therefor in Example 1. The substantial optical path length of the sample cell 15 is 50 mm as that of Example 1. A driver 19 outputs a control current with a modulation signal superimposed thereon to the solenoid coil 20 as the Faraday cell driver 9 used in Example 1. Other constitutional elements function in the same manner as those of the polarimeter of Example 1.

The angles of rotation attributed to pure water and glucose aqueous solutions respectively with concentrations of 1000 mg/dl and 2000 mg/dl were determined in the following manner by the use of the polarimeter of this example.

It was previously set as standard (or reference) in such a manner that the output signals from the lock-in amplifier 11, i.e., the values of the signal "S" shown in the equation (5) become zero at an injection current into the solenoid coil 20 of 0.02 A for the pure water having no optical activity, at 1.01 A for the glucose aqueous solution with a concentration of 1000 mg/dl, and at 2.00 A for the glucose aqueous solution with a concentration of 2000 mg/dl, respectively.

First, the control current varied discretely as −1.5 A, 0 A, and 1.5 A in 1.5 A intervals for every second was supplied to the solenoid coil 20 after superimposing a modulation signal with an amplitude of 0.001 A and a frequency of 1.3 kHz thereon. It is noted that the time constant of the lock-in amplifier 11 was set at 100 milliseconds.

Further, the stable output signal from the lock-in amplifier 11 after a lapse of one second from the start of supply of the control current at each current value was taken as a signal "S" with respect to the control current. The results are shown in FIG. 4 and Table 3.

TABLE 3

| Control current [A] | Signal "S" [V] | | |
|---|---|---|---|
| | Pure water | Glucose aqueous solution 1000 mg/dl | Glucose aqueous solution 2000 mg/dl |
| −1.5 | −0.304 | −0.480 | −0.700 |
| 0 | 0.040 | −0.205 | −0.320 |
| 1.5 | 0.290 | 0.107 | −0.085 |

Figure 4:
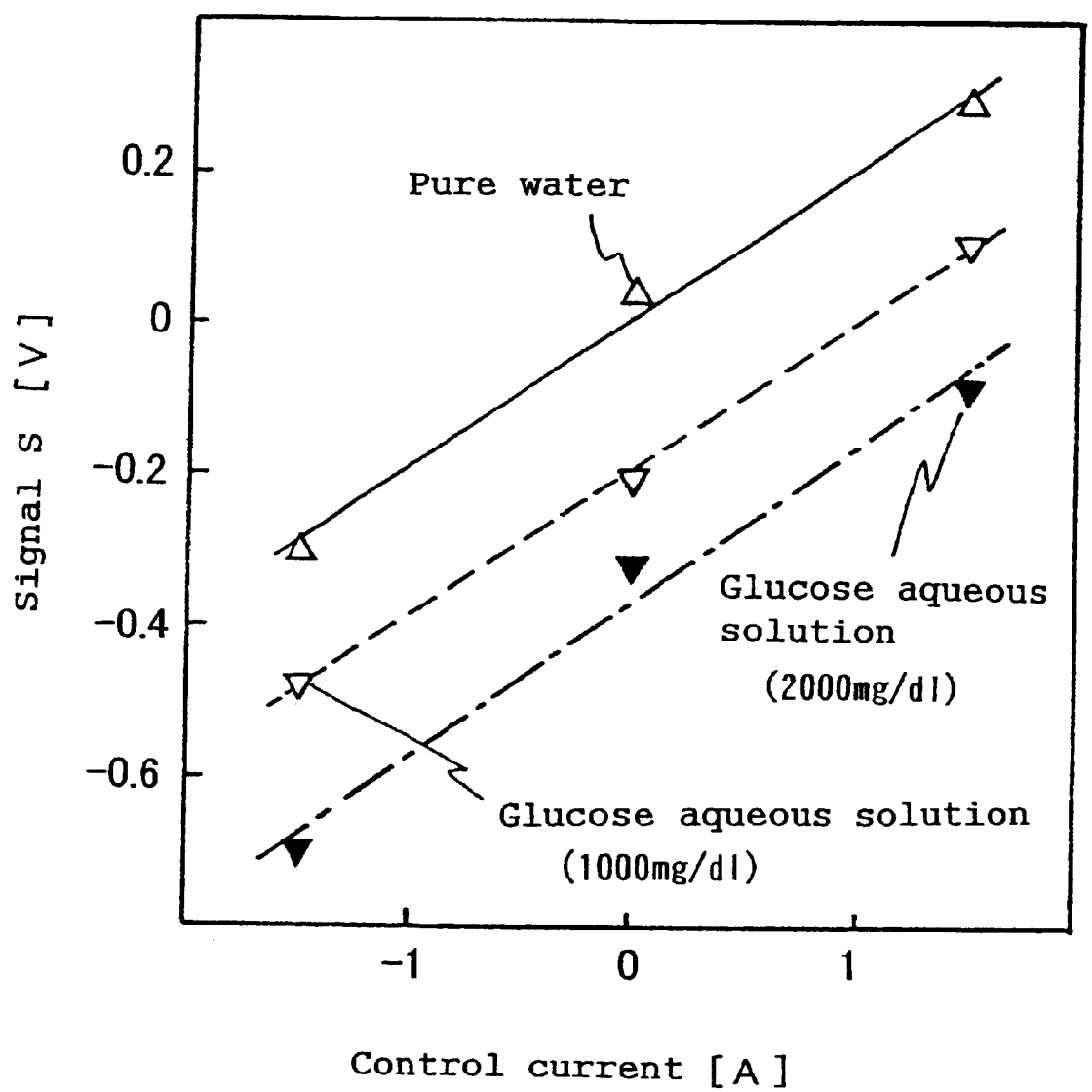
FIG. 4 is a characteristic diagram showing the relation between a control signal to be injected into the solenoid coil obtained in the embodiment and the intensity of a signal "S" outputted from a lock-in amplifier.

Herein, each straight line in FIG. 4 is a regression line obtained by the least squares method. If the control current is used as a criterion variable "X" and the signal "S" is used as a dependent variable "Y", the regression lines for the specimens are represented by the following equations (12), (13), and (14), respectively:

Pure water: $Y = 0.00867 + 0.198 \times X$ (12)

Glucose aqueous solution (1000 mg/dl): $Y = -0.193 + 0.196 \times X$ (13)

Glucose aqueous solution (2000 mg/dl): $Y = -0.368 + 0.205 \times X$ (14)

The control currents when the signal "S" becomes zero were calculated from the regression lines and are −0.0438 A for the pure water, and 0.985 A and 1.80 A for the glucose aqueous solutions with concentrations of 1000 mg/dl and 2000 mg/dl, respectively.

The correlation coefficient "R" with respect to the regression lines obtained was calculated and was 0.996 for the pure water. The correlation coefficients for the glucose aqueous solutions with concentrations of 1000 mg/dl and 2000 mg/dl were 0.999 and 0.991, respectively. These values serve as criteria for the fit thereof with their respective regression lines. This indicates that, the closer to 1 the absolute value of "R" is, the higher the fit between the data obtained and the regression line is.

When the correlation coefficient "R" is smaller than a prescribed value, for example, when R<0.995, a high measuring accuracy can be obtained by nullifying the measured results.

The differences of the control current values obtained from the regression lines from their respective predetermined values were calculated and were −0.0638 A for the pure water, and −0.025 A and −0.2 A for the glucose aqueous solutions with concentrations of 1000 mg/dl and 2000 mg/dl, respectively. These results indicate that the larger the correlation coefficient "R" is, the smaller the error from the predetermined value is.

Further, according to Example 1, since the overall time taken to sweep the control current is required to be sufficiently longer as compared with the time constant of the lock-in amplifier, a longer time is required for measurement in order to ensure a high S/N ratio. In contrast, according to this example, it is sufficient if the time between the start of supplying the control current and the determination of the signal "S" value at each discrete measuring point is set to be 7 to 8 times larger than the time constant of the lock-in amplifier, and a measurement with high accuracy is achieved for a shorter time.

As described above, according to this example, the angle of rotation can be measured with high accuracy and for a shorter time for specimens with a wider range of concentrations. Further, by detecting and eliminating the measured results with large errors, the measurement is ensured to have accuracy.

EXAMPLE 3

In this example, a description will be given to a method of urinalysis, i.e., a method of determining a glucose concentration in a urine or a urine sugar value utilizing the method of polarimetry according to Example 2.

The angles of rotation were determined under the same conditions as in Example 2 using the polarimeter of FIG. 3 used in Example 2 for urines 1 and 2 which had been previously determined by means of a urinalysis equipment to both have a concentration of albumin, i.e., protein in the urine of 10 mg/dl or less, and have glucose concentrations of 450 mg/dl and 655 mg/dl, respectively.

Further, the angles of rotation were additionally determined in the same manner for pure water and a glucose aqueous solution with a concentration of 1000 mg/dl. These results were used as standard for determining the glucose concentration.

Figure 5:
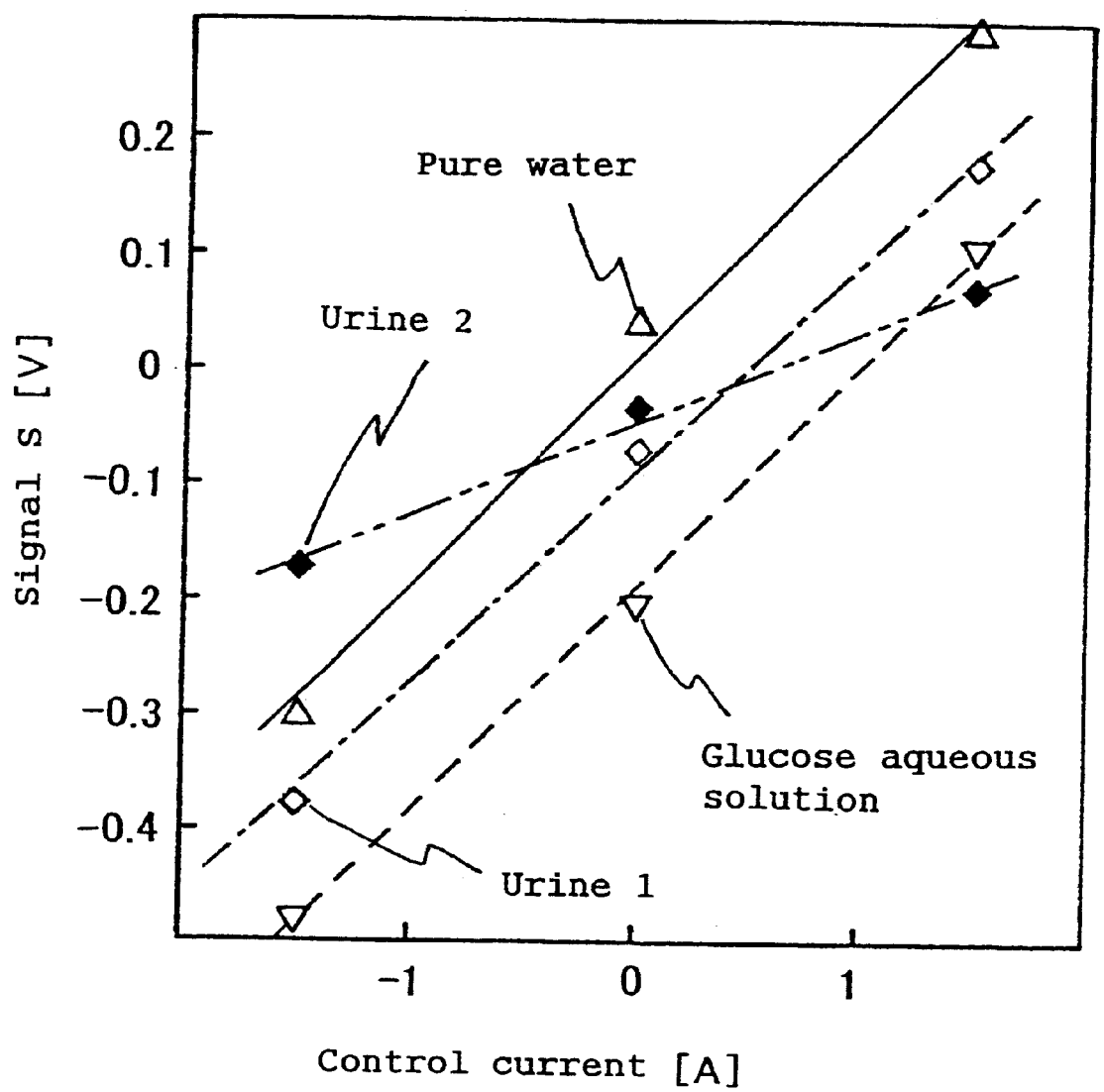
FIG. 5 is a characteristic diagram showing the relation between a control signal to be injected into the solenoid coil obtained in a still another embodiment and the intensity of a signal "S" outputted from the lock-in amplifier.
Figure 6:
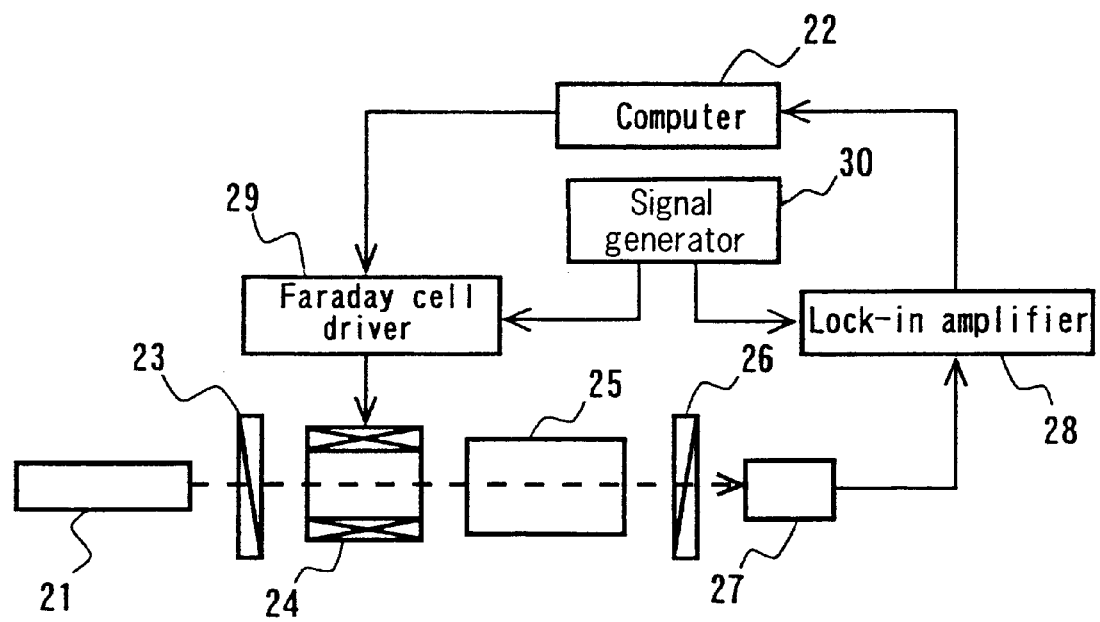
FIG. 6 is a block diagram showing the configuration of a conventional polarimeter.

The results obtained are shown in FIG. 5 and Table 4.

TABLE 4

| Control current [A] | Signal "S" [V] | | | |
|---|---|---|---|---|
| | Urine 1 | Urine 2 | Pure water | Glucose aqueous solution 1000 mg/dl |
| −1.5 | −0.380 | −0.175 | −0.304 | −0.480 |
| 0 | −0.0722 | −0.0365 | 0.040 | −0.205 |
| 1.5 | 0.175 | 0.0660 | 0.290 | 0.107 |

The regression lines where the control current is used as a criterion "X" and the signal "S" is used as a dependent "Y" for the urines 1 and 2 are expressed by the least squares method as the following equations (15) and (16), respectively:

$$\text{Urine 1: } Y = -0.0924 + 0.185 \times X \quad (15)$$

$$\text{Urine 2: } Y = -0.0485 + 0.0803 \times X \quad (16)$$

The control currents when the signal "S" becomes zero are found from these regression lines to be 0.499 A and 0.604 A for the urine 1 and the urine 2, respectively.

If the influence of the albumin in the urine is ignored, the respective control currents when the signal "S" becomes zero for the urine 1, the urine 2, pure water, and the glucose aqueous solution can be expressed as a linear function of the glucose concentrations of these specimens. Therefore, by using the control current amount "$X_0$" ($GL_0$) when the signal "S" is zero for pure water, and the control current amount "$X_0$" ($GL_{1000}$) when the signal "S" is zero for the glucose aqueous solution as standards, the urine glucose concentration "Co" can be calculated from the measured value "$X_0$" of the control current by using the following equation (17):

$$Co = (X_0 - X_0(GL_0)) \times 1000 / (X_0(GL_{1000}) - X_0(GL_0)) \quad (17)$$

$$= (X_0 - 0.02) \times 1000 / 0.99 \ [\text{mg/dl}]$$

From this equation, the glucose concentrations, i.e., urine sugar values are found to be 484 mg/dl and 590 mg/dl for the urines 1 and 2, respectively.

Table 5 shows the sums of squares of residuals "$S_E$" between the measured data and the regression formulae, standardized sums of squares of residuals "D" shown in the equation (8), and the correlation coefficients "R". The "D" is obtained by dividing the sum of squares of residuals "$S_E$" by the sum of squares of the dependent variable "Y" value (calculated value of the signal "S"), which is obtained by substituting the data of the control current amount into the criterion variable "X" of the regression line obtained.

$$D = S_E / \Sigma (a + bX)^2 \quad (8)$$

where the regression formula is Y=a+bX.

TABLE 5

| | Signal "S" [V] | | | |
|---|---|---|---|---|
| | Urine 1 | Urine 2 | Pure water | Glucose aqueous solution 1000 mg/dl |
| $S_E$ | $6.12 \times 10^{-4}$ | $2.16 \times 10^{-4}$ | $1.47 \times 10^{-3}$ | $2.28 \times 10^{-4}$ |
| D | $3.46 \times 10^{-3}$ | $5.98 \times 10^{-3}$ | $8.32 \times 10^{-3}$ | $8.03 \times 10^{-4}$ |
| R | 0.998 | 0.996 | 0.996 | 0.999 |

The comparison between the correlation coefficients indicates that the accuracy of the regression formula for the urine 1 is higher than that of the urine 2.

It is indicated that, the smaller the sum of squares of residuals is, the higher the accuracy of the regression formula is. However, the sum of squares of residuals tends to decrease with a decrease in an absolute value of the signal "S". Further, other elements such as light transmittance of the specimen exert an influence on the absolute value. Therefore, it is not advisable to conduct a comparison between the specimens by directly using the sums of squares of residuals. For this reason, use of the standardized sums of squares of residuals as the "D" facilitates the comparison between specimens.

Actually, as shown in Table 5, although the urine 2 has a smaller sum of squares of residuals than the urine 1, the regression formula for the urine 1 has a higher accuracy according to the correlation coefficient. This is due to the fact that the transmittance of the urine 2 is lower than that of the urine 1, and the absolute value of the signal "S" is small. However, it is indicated that the standardized sum of squares of residuals "D" and the correlation coefficient "R" function as criteria for accuracy irrespective of the magnitude of absolute value of the signal "S".

As described above, according to the present invention, there can be provided a method of polarimetry and a method of urinalysis which are capable of preventing the mixing of an error feared in a conventional method of polarimetry, in which the extinction point when the signal "S" becomes zero must be found while measuring the signal in a certain point. Futher, the method of polarimetry and the method of urinalysis according to the present invention can perform a stable and highly accurate measurement in a short time.

What is claimed is:

1. A method of polarimetry for allowing a light to be incident upon a specimen to be detected containing a spontaneous optical active substance, and determining an optical rotation attributed to said spontaneous optical active substance when said light transmits through said specimen, comprising the steps of:

(a) allowing a polarized light having a known plane of vibration to be incident upon said specimen while micro-vibrating said plane of vibration by a modulation signal with an angular frequency of ω;

(b) detecting a component having a specific plane of vibration out of said polarized light transmitted through said specimen by a photosensor;

(c) extracting a component with an angular frequency of ω out of an output signal from said photosensor by phase sensitive detection using said modulation signal as a reference signal; and (d) calculating an angle of rotation attributed to said specimen based on 3 or more groups of data including a relative angle formed between a plane of vibration of said light incident upon said specimen and said specific plane of vibration of the light to be detected by said photosensor, and an intensity of said component with an angular frequency of ω obtained at said relative angle.

2. The method of polarimetry in accordance with claim 1, wherein in said step (a), said relative angle is varied by continuously rotating the plane of vibration of said polarized light incident upon said specimen.

3. The method of polarimetry in accordance with claim 1, wherein in said step (a), said relative angle is varied by discretely changing the plane of vibration of said polarized light incident upon said specimen.

4. The method of polarimetry in accordance with claim 1, wherein in said step (d), a linear regression formula is formed based on said data by using said relative angle as a criterion variable and using the intensity of said component with an angular frequency of $\omega$ as a dependent variable, and an angle of rotation attributed to said specimen is calculated based on the regression formula obtained.

5. The method of polarimetry in accordance with claim 1, wherein in said step (a), said relative angle is varied by rotating the plane of vibration of said polarized light incident upon said specimen by the optical Faraday effect.

6. The method of polarimetry in accordance with claim 5, wherein in said step (d), a linear regression formula is formed based on said data by using a magnitude of a magnetic field for obtaining said relative angle or a current amount for generating said magnetic field as a criterion variable, and using the intensity of said component with an angular frequency of $\omega$ as a dependent variable, and an angle of rotation attributed to said specimen is calculated based on the regression formula obtained.

7. A method of polarimetry for allowing a light to be incident upon a specimen to be detected containing a spontaneous optical active substance and a magneto-optical active substance and applying a magnetic field to said specimen, thereby rotating a plane of vibration of said light transmitting through said specimen by an optical Faraday effect, and determining an optical rotation attributed to said spontaneous optical active substance when said light transmits through said specimen based on a magnitude of rotation of said light caused by said magnetic field, comprising the steps of:

(a) allowing a polarized light having a known plane of vibration to be incident upon said specimen while micro-vibrating said plane of vibration by a modulation signal with an angular frequency of $\omega$;

(b) detecting a component having a specific plane of vibration out of said polarized light transmitted through said specimen by a photosensor;

(c) extracting a component with an angular frequency of $\omega$ out of an output signal from said photosensor by phase sensitive detection using said modulation signal as a reference signal; and (d') calculating an angle of rotation attributed to said specimen based on 3 or more groups of data including a magnitude of said magnetic field and an intensity of said component with an angular frequency of w obtained at said magnitude of said magnetic field.

8. The method of polarimetry in accordance with claim 7, wherein in said step (a), said plane of vibration of said light is continuously rotated by the optical Faraday effect.

9. The method of polarimetry in accordance with claim 7, wherein in said step (a), said plane of vibration of said light is discretely rotated by the optical Faraday effect.

10. The method of polarimetry in accordance with claim 7, wherein in said step (d'), a linear regression formula is formed based on said data by using the magnitude of said magnetic field or a current amount for generating said magnetic field as a criterion variable and using the intensity of said component with an angular frequency of $\omega$ as a dependent variable, and an angle of rotation attributed to said specimen is calculated based on the regression formula obtained.

11. The method of polarimetry in accordance with claim 4, wherein in said step (d), said regression formula is calculated by using a least squares method.

12. The method of polarimetry in accordance with claim 4, wherein step (d) comprises a step of estimating the measurement to be effective when reliability of said regression formula is higher than a predetermined value.

13. The method of polarimetry in accordance with claim 12, wherein a sum of squares of residuals $S_E$, a value D obtained by dividing said sum of squares of residuals $S_E$ by the sum of squares of the intensity values of said component with an angular frequency of $\omega$, which is obtained by substituting data corresponding to the criterion variable of said regression formula, or a correlation coefficient R shown in the following formulae is used as criterion evaluation of said reliability:

$$S_E = \sum_{i=1}^{n} \{Y_i - (a + bX_i)\}^2$$

$$D = \frac{S_E}{\sum_{i=1}^{n} (a + bX_i)^2}$$

$$R = \frac{\sum_{i=1}^{n} [(X_i - \overline{X}) \times (Y_i - \overline{Y})]}{\sqrt{\sum_{i=1}^{n} (X_i - \overline{X})^2 \times \sum_{i=1}^{n} (Y_i - \overline{Y})^2}}$$

where the regression formula is expressed as Y=a+bX, $X_i$ (i=1 to n) is the data for the criterion variable "X" of the regression formula, $Y_i$ (i=1 to n) is the data for the dependent variable "Y" of the regression formula, $\overline{X}$ is the mean value of $X_i$, and $\overline{Y}$ is the mean value of $Y_i$.

14. A method of urinalysis for detecting a concentration of a spontaneous optical active substance in a urine by using said method of polarimetry in accordance with claim 1.

15. The method of polarimetry in accordance with claim 6, wherein in said step (d), said regression formula is calculated by using a least squares method.

16. The method of polarimetry in accordance with claim 10, wherein in said step (d'), said regression formula is calculated by using a least squares method.

17. The method of polarimetry in accordance with claim 6, wherein step (d) comprises a step of estimating the measurement to be effective when reliability of said regression formula is higher than a predetermined value.

18. The method of polarimetry in accordance with claim 10, wherein step (d') comprises a step of estimating the measurement to be effective when reliability of said regression formula is higher than a predetermined value.

19. A method of urinalysis for detecting a concentration of a spontaneous optical active substance in a urine by using said method of polarimetry in accordance with claim 7.

* * * * *